US005137887A

United States Patent [19]
Hashimoto et al.

[11] Patent Number: 5,137,887
[45] Date of Patent: Aug. 11, 1992

[54] SALTS OF OPTICALLY ACTIVE 4-HYDROXY-8(3-LOWER ALKOXY-4-PHENYLSULFINYLPHENYL)-PYRAZOLO(1,5-A)-1,3,5- TRIAZINES AND A PROCESS FOR PRODUCTION THEREOF

[75] Inventors: Kinji Hashimoto, Naruto; Masatoshi Inai, Tokushima, both of Japan

[73] Assignee: Otsuka Pharmaceutical Factory, Inc., Tokushima, Japan

[21] Appl. No.: 567,632

[22] Filed: Aug. 15, 1990

[30] Foreign Application Priority Data

Aug. 25, 1989 [JP] Japan .................................. 1-219181
Jul. 6, 1990 [JP] Japan .................................. 2-179852

[51] Int. Cl.$^5$ .................... C07D 487/04; A61K 31/53
[52] U.S. Cl. ...................................... 514/246; 544/219
[58] Field of Search ......................... 544/219; 514/246

[56] References Cited

FOREIGN PATENT DOCUMENTS 0269859 6/1988 European Pat. Off. .

OTHER PUBLICATIONS

Fujii et al., Chemical Abstracts, vol. 108, entry 211,092p (1988).
Hawley's Condensed Chemical Dictionary, Eleventh Edition, 1987, pp. 584–585.

Primary Examiner—John M. Ford
Attorney, Agent, or Firm—Wegner, Cantor, Mueller & Player

[57] ABSTRACT

The invention relates to a salt selected from group consisting of alkali metal salts and alkaline earth metal salts of an optically active form of a 4-hydroxy-8-(3-lower alkoxy-4-phenylsulfinylphenyl)pyrazolo[1,5-a]-1,3,5-triazine, a process for producing said optically active compound or salt thereof, and a pharmaceutical composition, such as an antipodagric agent, comprising an effective amount of the salt together with a pharmaceutically acceptable nontoxic carrier.

14 Claims, No Drawings

SALTS OF OPTICALLY ACTIVE 4-HYDROXY-8(3-LOWER ALKOXY-4-PHENYLSULFINYLPHENYL)-PYRAZOLO(1,5-A)-1,3,5- TRIAZINES AND A PROCESS FOR PRODUCTION THEREOF

The present invention relates to a salt selected from among alkali metal salts and alkaline earth metal salts of an optically active 4-hydroxy-8-(3-lower alkoxy-4-phenylsulfinylphenyl)pyrazolo[1,5-a]-1,3,5-triazine, and processes for producing said optically active compound and salts thereof.

It is well known that 4-hydroxy-8-(3-lower alkoxy-4-phenylsulfinylphenyl)pyrazolo[1,5-a]-1,3,5-triazines are pharmaceutically useful compounds. The method for optical resolution of these compounds heretofore been proposed is a method by using a chromatographic technique involving the use of an optically active column. This procedure requires a large volume, namely about 1,300 to 1,600 l, of a solvent for elution of one gram of the desired compound. Therefore, the fractional isolation of an optically active form of the compound on a production scale involves much technical difficulty and, hence, requires much time and cost. To the best of the present inventors' knowledge, there is no other reported method for optical resolution other than the chromatographic technique mentioned just above.

It is known that the solubility of a hardly soluble compound can generally be increased by converting it to an alkali metal or other salt but the racemic form of said triazine compound can hardly be rendered soluble by conversion to an alkali metal or alkaline earth metal salt. In other words, it is difficult to process this compound into an injectable solution, for instance, thus imposing a serious limitation on its pharmaceutical application.

It is an object of the present invention to provide a novel process for producing and isolating an optically active triazine compound at low cost and in a short time, particularly a method for asymmetric synthesis of the same compound.

It is another object of the invention to provide a salt of said optically active triazine compound which overcomes the above-mentioned difficulty to process into an injectable pharmaceutical product.

As the result of their assiduous and diligent research into this field of technology, the inventors of the present invention succeeded in establishing a method of asymmetric synthesis to be described hereinafter and found that certain salts of the resulting optically active compound exhibit excellent solubility which can hardly be anticipated from the knowledge about salts of the usual racemic compound.

Thus, in accordance with the present invention, there is provided a salt selected from the group consisting of alkali metal salts and alkaline earth metal salts of an optically active 4-hydroxy-8-(3-lower alkoxy-4-phenylsulfinylphenyl)pyrazolo[1,5-a]-1,3,5-triazine compound of the formula

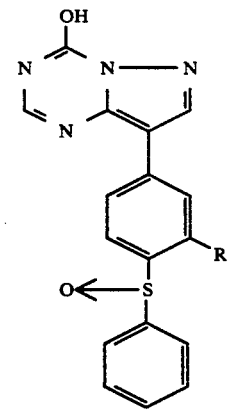

(1)

wherein R means a lower alkoxy group.

In accordance with the present invention, there is further provided a process for producing an optically active form of a triazine compound of the above formula (1) or a salt selected from the group consisting of alkali metal salts and alkaline earth metal salts of said optically active form of the compound which comprises reacting a 4-hydroxy-8-(3-lower alkoxy-4-phenylthiophenyl)pyrazolo[1,5-a]-1,3,5-triazine of the formula

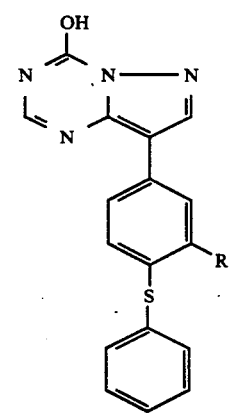

(2)

wherein R is a lower alkoxy group with a halogen-containing oxidizing agent in the presence of an optically active cyclic compound of the general formula

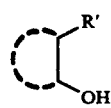

(3)

wherein R' is a lower alkyl group, a phenyl group or a phenyl-lower alkyl group and either treating the reaction product with water or a metal hydroxide or subjecting the same to heat treatment, if necessary followed by reacting the same with an alkali metal hydroxide or alkaline earth metal hydroxide to give a salt.

The present invention is further directed to a process for producing an optically active form of a 4-hydroxy-8-(3-lower alkoxy-4-phenylsulfinylphenyl)pyrazolo[1,5-a]-1,3,5-triazine compound or a salt selected from the group consisting of alkali metal salts and alkaline earth metal salts of the same compound which comprises seeding a solution of the racemic mixture of a triazine compound (1) with seed crystals composed exclusively of one optically active form of the same triazine compound to cause crystallization of the corresponding optical form and isolating the resulting crystals, if necessary followed by treating the same with an alkali metal hydroxide or alkaline earth metal hydroxide to give a salt.

Referring to the above respective formulas, the lower alkyl group denoted by R' includes, among others, methyl, ethyl, propyl, isopropyl, butyl, tert-butyl, pentyl, isopentyl, 2,2-dimethylpropyl, 1-methylbutyl, hexyl, 4-methylpentyl, 3-methylpentyl, 2-methylpentyl, 1-methylpentyl, 3,3-dimethylbutyl, 2,2-dimethylbutyl and 1,3-dimethylbutyl. The phenyl-lower alkyl group includes, among others, benzyl, α-phenethyl, β-phenethyl, 1-phenylpropyl, 2-phenylpropyl, 3-phenylpropyl, 1-methyl-1-phenylethyl, 1-methyl-2-phenylethyl, 1-phenylbutyl, 2-phenylbutyl, 3-phenylbutyl, 4-phenylbutyl, 1-methyl-1-phenylpropyl, 1-methyl-2-phenylpropyl, 2-methyl-2-phenylpropyl, 1-methyl-3-phenylpropyl, 1-phenylpentyl, 2-phenylpentyl, 3-phenylpentyl, 4-phenylpentyl, 5-phenylpentyl, 1-methyl-1-phenylbutyl, 1,2-dimethyl-1-phenylpropyl, 1-methyl-2-phenylbutyl, 1-methyl-3-phenylbutyl, 1-methyl-4-phenylbutyl, 2-methyl-2-phenylbutyl, 2-methyl-3-phenylbutyl, 2-methyl-4-phenylbutyl, 3-methyl-3-phenylbutyl, 1-phenylhexyl, 2-phenylhexyl, 3-phenylhexyl, 4-phenylhexyl, 5-phenylhexyl, 6-phenylhexyl, 1-methyl-1-phenylpentyl, 1-ethyl-1-phenylbutyl, 1-methyl-2-phenylpentyl, 1-methyl-3-phenylpentyl, 1-methyl-4-phenylpentyl, 1-methyl-5-phenylpentyl, 2-methyl-2-phenylpentyl, 3-methyl-2-phenylpentyl, 3-ethyl-2-phenylpentyl, and 4-methyl-4-phenylpentyl.

The lower alkoxy group denoted by R includes, among others, methoxy, ethoxy, propoxy, isopropoxy, butoxy, tert-butoxy, pentyloxy, isopentyloxy, 2,2-dimethylpropoxy, 1-methylbutoxy, hexyloxy, 4-methylpentyloxy, 3-methylpentyloxy, 2-methylpentyloxy, 1-methylpentyloxy, 3,3-dimethylbutoxy, 2,2-dimethylbutoxy and 1,3-dimethylbutoxy.

The process for production of an optically active form of a triazine compound (1) according to the invention (method of asymmetric synthesis) can be represented by the reaction scheme presented below. This process consists of a first reaction stage which comprises reacting a 4-hydroxy-8-(3-lower alkoxy-4-phenylthiophenyl)pyrazolo[1,5-a]-1,3,5-triazine [Compound (2)] with a halogen-containing oxidizing agent in the presence of an optically active cyclic compound of general formula (3) and a second reaction stage which comprises either reacting the reaction mixture obtained in the first stage with water or a metal hydroxide or subjecting it to heat treatment.

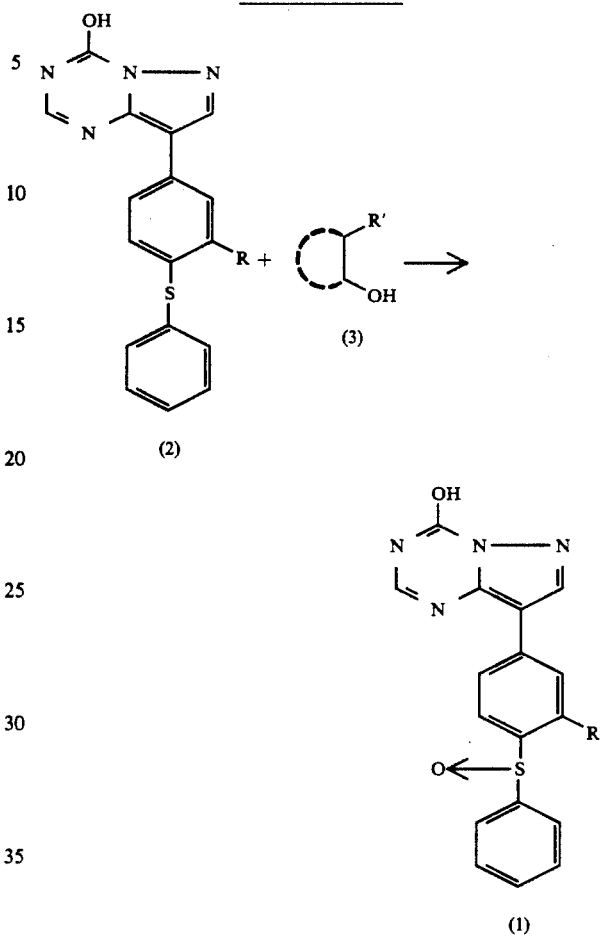

Reaction scheme wherein R and R' are respectively as defined hereinbefore.

The cyclic compound (3) to be used in the first stage shown in the above scheme is an alcohol derivative and this alcohol derivative is an optically active secondary alcohol. The substituent R' on this alcohol derivative should be present in α-position with respect to the alcoholic hydroxy (OH) group and can be selected from the specific groups mentioned hereinbefore. However, the higher the bulk of the substituent, the greater is the improvement in asymmetric yield. Therefore, when a lower alkyl group is chosen for said substituent R', for instance, the branched-chain group is preferred to the straight-chain group. The cyclic nucleus of said alcohol derivative is a 4- to 8-membered ring, preferably a 5- to 6-membered ring, and may be a bicyclo structure or a fused ring structure. This cyclic nucleus may be a saturated or unsaturated ring consisting exclusively of carbon atoms or even a hetero atom-containing ring meeting the above definition. Specific examples of said alcohol derivative are (−)-menthol, (+)-menthol, (−)-8-phenylmenthol, (+)-8-phenylmenthol, (+)-2-tert-butyl-1-indanol, (−)-borneol, [(1S)-endo]-(−)-borneol, (1S,2S)-(+)-1-hydroxy-2-methyl-3-cyclopentene, (1S,2S)-(+)-1-hydroxy-2-methylcyclohexane, (1S,2R)-(+)-1-hydroxy-2-phenylcyclohexane, (1S,2R)-(+)-1-hydroxy-2-phenylcyclopentane and (1S,2R)-(+)-3-hydroxy-2-phenyltetrahydrofuran.

Among these alcohol derivatives, optically active menthol is preferred from cost consideration.

The reaction between said compound (2) and compound (3) can be carried out by dissolving the above respective compounds and an organic base in an appropriate solvent, cooling the solution and permitting a halogen-containing oxidizing agent, such as t-butylhypochlorite, 1-chlorobenzotriazole, N-chlorosuccinimide or the like, to act upon the solution.

The common inert solvents such as, typically, N,N-dimethylformamide, acetonitrile, dichloromethane, etc., can be used independently or in combination. The organic base may typically be pyridine or triethylamine, for instance. While the proportions of the above respective compounds are not critical, the proportion of compound (3) may be about 20 to 0.8 mole equivalent, preferably about 10 to 1 mole equivalents and the proportion of said organic base may be about 1 to 3 mole equivalents, preferably about 1 to 1.5 mole equivalents, both relative to compound (2). Incidentally, the above organic base is used to prevent the pH of the reaction system from being shifted toward the acidic side and the addition of the base precludes the production of the racemic form of the end product, that is to say the reduction of asymmetric yield.

The solution of said compound (2), compound (3) and organic base is cooled generally to about $-40°$ C. to $-10°$ C. and preferably to about $-30°$ C. to $-20°$ C. If the temperature of the solution is much higher, the asymmetric yield of the final product tends to be undesirably decreased.

The reagent such as t-butyl hypochlorite is added for the purpose of converting compound (2) to a sulfonium salt and its proportion based on compound (2) is generally about 1 to 2 mole equivalents and preferably about 1 to 1.3 mole equivalents.

As the second stage reaction following the first stage described above, either of the following two methods A and B can be employed.

In one (method A) of those two methods, the reaction mixture obtained in the first stage is stirred with cooling at a temperature not over $0°$ C., preferably between about $-30°$ C. and $-25°$ C., for about 30 minutes to 3 hours and, then, either water or an aqueous solution of a metal hydroxide is added. The aqueous layer is made weakly acidic with an organic acid to thereby give the desired compound. As examples of the metal hydroxide to be used in this method, there may be mentioned alkali metal hydroxides such as sodium hydroxide, potassium hydroxide, etc. and alkaline earth metal hydroxides such as calcium hydroxide, magnesium hydroxide and so on. The above metal hydroxide is used in a concentration of generally about 5 to 30 w/w percent and preferably about 8 to 25 w/w percent. The reaction temperature may range from about $-40°$ C. to $+20°$ C. and preferably from about $-30°$ C. to $0°$ C.

After completion of the reaction, water is added to the reaction mixture to have the product compound transferred into the aqueous layer and, then, an organic acid such as acetic acid, citric acid, tartaric acid or the like is added to give the desired optically active 4-hydroxy-8-(3-lower alkoxy-4-phenylsulfinylphenyl)-pyrazolo[1,5-a]-1,3,5-triazine.

The other method (method B) for implementing the second stage comprises heating the reaction mixture obtained in the first stage at about $50°$ C. for about 2 hours, then adding an 8-25 w/w % aqueous alkali solution to have the product compound transferred into the aqueous layer, and adding an organic acid to this aqueous layer to make it weakly acidic and thereby give the desired compound.

For examples of the organic acid to be used in this method, reference may be made to the acids mentioned hereinbefore. Particularly, this method gives the other enantiomer to that obtainable by the above method A.

The inventors of the present invention found that a 50:50 mixture of the two enantiomers of a 4-hydroxy-8-(3-lower alkoxy-4-phenylsulfinylphenyl)pyrazolo-[1,5-a]-1,3,5-triazine forms a racemic mixture and that when seed crystals composed exclusively of one of the optically active compounds (enantiomers) are added to such a mixture for recrystallization, only the optically active compound corresponding to the enantiomer constituting the seed crystals is selectively crystallized, thus permitting selective recovery of the particular optically active compound in a very expedient manner and in high purity and good yield. The present invention, therefore, provides such a novel process for isolating an optically active compound, too.

As the starting material for this selective recovery of an optically active compound in accordance with the invention, a solution of such a racemic 4-hydroxy-8-(3-lower alkoxy-4-phenylsulfinylphenyl)pyrazolo[1,5-a]-1,3,5-triazine in an appropriate solvent can be employed. While chloroform-methanol may be mentioned as a typical example of the solvent mentioned just above, various other recrystallization solvents such as dichloroethane-methanol, dichloroethane-ethanol, N,N-dimethylformamide-water, ethyl acetate-methanol, etc. may likewise be employed. As the seed crystals with which the above solution is seeded, crystals of any optically active compound that has been obtained by the asymmetric synthesis according to the invention can be advantageously employed but this is not an exclusive choice. Thus, crystals of the optically active compound separated by the conventional column chromatographic method can also be employed. The amount of such seed crystals for seeding may be about 1/2000 to 1/100 of the amount of the racemic mixture and the suitable amount of crystals to be produced is generally up to about 30 percent of the total amount of the racemic mixture.

In this manner, the desired optically active compound can be selectively crystallized.

The optically active compound produced by the above methods can be further purified by the conventional procedure.

The optically active 4-hydroxy-8-(3-lower alkoxy-4-phenylsulfinylphenyl)pyrazolo[1,5-a]-1,3,5-triazine thus obtained can be converted to a pharmaceutically acceptable salt by reacting it with an appropriate base. The salt mentioned above includes, among others, alkali metal salts such as lithium salt, sodium salt, potassium salt, etc. and alkaline earth metal salts such as berrylium salt, magnesium salt, calcium salt and so on.

Unlike the salt of the corresponding racemic compound, the salt of the optically active compound exhibits remarkably higher solubility which is far beyond imagination from the knowledge about the racemic compound. Thus, the experiment performed by the inventors revealed, for instance, that whereas the solubility of the sodium salt of the above racemic compound in water is about 0.2 w/w %, the solubility of the sodium salt of the optically active compound is as high as not less than 50 w/w %. With regard to solubilities in physiological saline, too, whereas the solubility of the sodium salt of the racemic compound is about 0.08 w/w %, the solubility of the sodium salt of the optically active compound is as high as not less than 50 w/w %. Thus, in accordance with the present invention, very much more soluble salts of the optically active compound can be provided.

The above-mentioned salts can each be produced by reacting the optically active compound obtained as above with an appropriate base. The base to be used as the salt-forming agent is preferably a metal hydroxide, such as hydroxides of alkali metals of alkaline earth metals, although carbonates, bicarbonates or alkoxides of the above-mentioned metals may likewise be employed. The salt-forming reaction can be carried out in the routine manner and the resulting salt can be isolated and purified by procedures similar to those described for the free compound.

The optically active 4-hydroxy-8-(3-lower alkoxy-4-phenylsulfinylphenyl)pyrazolo[1,5-a]-1,3,5-triazine and salts obtainable by the working of the present invention invariably have xanthine oxidase inhibitory activity and are of value as pharmaceutical agents, such as antipodagric (gout suppression) and other drugs. In pharmaceutical applications, the above salt of optically active compound can be more easily and advantageously processed into various dosage forms, e.g. concentrated injectable solutions, than the corresponding free compound, particularly because of its enhanced solubility.

The present invention is further directed to a pharmaceutical composition containing at least one species of the above-mentioned optically active 4-hydroxy-8-(3-lower alkoxy-4-phenylsulfinylphenyl)pyrazolo[1,5-a]-1,3,5-triazine or salt thereof as an active ingredient together with a pharmaceutically acceptable nontoxic carrier for application to man and other animals.

Examples of said carrier are conventional diluents and excipients such as fillers, extenders, binders, wetting agents, disintegrating agents, surfactants and lubricants. These carriers are selected according to the intended unit dosage form.

Dosage forms are selected according to the therapeutical purpose. Typical examples of such dosage form are tablets, pills, powders, solutions, suspensions, emulsions, granules, capsules, suppositories, injections (solutions, suspensions, etc.) and the like. Carriers useful for shaping the medicinal preparation into tablets are lactose, purified sugar, sodium chloride, glucose, urea, starch, calcium carbonate, kaolin, crystalline cellulose, silicic acid, potassium phosphate and like excipients; water, ethanol, propanol, simple syrup, glucose solution, starch solution, gelatin solution, carboxymethylcellulose, hydroxypropylcellulose, methylcellulose, polyvinylpyrrolidone and like binders; sodium carboxymethylcellulose, carboxymethylcellulose calcium, low-substituted hydroxypropylcellulose, dried starch, sodium alginate, agar powder, laminaran powder, sodium bicarbonate, calcium carbonate and like disintegrating agents; polyoxyethylene sorbitan fatty acid esters, sodium laurylsulfate, monoglyceryl stearate and like surfactants; purified sugar, stearin, cacao butter, hydrogenated oils and like disintegration inhibitors; quaternary ammonium base, sodium laurylsulfate and like absorption accelerators; glycerol, starch and like wetting agents; starch, lactose, kaolin, bentonite, colloidal silica and like absorbents; purified talc, stearic acid salts, boric acid powder, poly(ethylene glycol) and like lubricants and so on. If necessary, such tablets can be further coated with a usual coating composition to obtain coated tablets, for example sugar-coated tablets, gelatin-coated tablets, enteric-coated tablets, film-coated tablets, or double-layer tablets, multilayered tablets, etc. Carriers useful for shaping the composition into pills are glucose, lactose, starch, cacao butter, hydrogenated vegetable oils, kaolin, talc and like excipients; gum arabic powder, tragacanth gum powder, gelatin, ethanol and like binders; laminaran, agar powder and like disintegrating agents and so on.

Carriers for shaping the composition into suppositories are poly(ethylene glycol), cacao butter, higher alcohols, esters of higher alcohols, gelatin, semisynthetic glyceride and the like. Capsules are usually formed by the conventional method, for example by mixing the compound of the invention as an active ingredient with the carriers as exemplified above, and encapsulating the mixture into hard-gelatin capsules, soft-gelatin capsules or the like. In forming injectable solutions, emulsions and suspensions, they are sterilized and preferably made isotonic to the blood. Diluents useful for this purpose are, for example, water, ethanol, polyethylene glycol, propylene glycol, ethoxylated isostearyl alcohol, polyoxylated isostearyl alcohol, polyoxyethylene sorbitan fatty acid esters and the like. In preparing isotonic solutions, sodium chloride, glucose or glycerol may be added in an amount sufficient to make the solution isotonic. The pharmaceutical composition of the invention may contain the common solubilizer, buffer, soothing agent and other additives. When required, the preparation of the invention may further contain colorants, preservatives, flavoring agents, sweetening agents and other medicaments. In the molding of ointments, inclusive of pastes, creams, gels, etc., such diluents are white petrolatum, paraffin, glycerol, cellulose derivatives, polyethylene glycol, silicone, bentonite, etc. can be employed.

The proportion of the active compound in such pharmaceutical composition is not critical but can be selected from a broad range but it is generally recommendable to incorporate about 5 to 300 mg in the pharmaceutical composition. Particularly since the salt of optically active compound according to the invention is very freely soluble, it can be easily worked into homogeneous solutions, e.g. injections, which may contain this active ingredient in a concentration ranging from about 0.1 to 10%.

There is virtually no limitation on the method of administration of the above pharmaceutical composition and a suitable treatment regimen can be selected according to the dosage form, patient age, sex and other characteristics, severity of illness and so on. For example, while the tablets, pills, solution, suspension, emulsion, granules and capsules are orally administered, the injectable solutions can be administered intravenously in admixture with ordinary replacement fluids or infusions, such as glucose, amino acid and other infusions. If required, the injectable solution can be administered intramuscularly, intradermally, subcutaneously or intraperitoneally. The suppositories can be administered intrarectally.

The dosage depends on the administration route, patient age, sex and other characteristics, severity of illness and other conditions. Generally, however, the dosage as the active compound of the invention may range from about 0.5 to 20 mg per kilogram body weight/day and can be administered in 1 to 4 divided doses a day.

The following examples of production of the optically active compound and salt of the invention and the following working examples are intended to illustrate the invention in further detail.

EXAMPLE 1

In 600 ml of N,N-dimethylformamide (DMF) were dissolved 60 g of 4-hydroxy-8-(3-methoxy-4-phenylthiophenyl)pyrazolo[1,5-a]-1,3,5-triazine, 110 g of l-(−)-menthol and 17.2 ml of pyridine and the mixture was cooled to −25° C. to −30° C. Then, 21.2 g of t-butyl hypochlorite was added dropwise and the mixture was stirred at −25° C. to −30° C. for 1 hour. Then, 750 ml of 20% aqueous sodium hydroxide solution was added at −30° C. to −10° C., followed by addition of 2 l of water. The reaction mixture was washed with ethyl acetate and the aqueous layer was made weakly acidic with 500 g of citric acid to cause crystallization. The crystals are collected by filtration, rinsed with water and then washed with ethanol and dried in the air. The procedure gave 57 g of crude crystals of 4-hydroxy-8-(3-methoxy-4-phenylsulfinylphenyl)pyrazolo[1,5-a]-1,3,5-triazine. The optical rotation of this product was $[\alpha]_D^{20} = -75°$ (c=0.5, DMF).

The above crystals were recrystallized from chloroform-methanol (1:1) three times and, then, heated with ethyl acetate under reflux for 30 minutes. After cooling, the crystals separating out were collected by filtration. This procedure gave 16 g of (−)-4-hydroxy-8-(3-methoxy-4-phenylsulfinylphenyl)pyrazolo-[1,5-a]-1,3,5-triazine (yield 25.5%, optical purity ≥99%).

The optical rotation of this product was $[\alpha]_D^{20} = -174°$ (c=0.5, DMF).

The melting point was 265°-268° C. (decomp.) and the elemental analysis (for $C_{18}H_{14}O_3N_4S_1$, mol. wt. 366.40) was as follows.

Calcd.: C, 59.00; H, 3.85; N, 15.29. Found: C, 58.74; H, 3.55; N, 14.99.

The same procedure as above was followed except that d-(+)-menthol was used in lieu of l-(−)-menthol to give 15 g of (+)-4-hydroxy-8-(3-methoxy-4-phenylsulfinylphenyl)pyrazolo[1,5-a]-1,3,5-triazine (yield 24%, optical purity ≥99%).

Optical rotation, $[\alpha]_D^{20} = +174°$ (c=0.5, DMF)
Melting point: 265°-268° C. (decomp.)
Elemental analysis (for $C_{18}H_{14}O_3N_4S_1$, mol. wt. 366.40) Calcd.: C, 59.00; H, 3.85; N, 15.29. Found: C, 58.74; H, 3.64; N, 14.93.

EXAMPLE 2

In a mixed solution prepared from 50 ml of ethanol, 10 ml of water and 145 mg of sodium hydroxide were dissolved 1.3 g of (−)-4-hydroxy-8-(3-methoxy-4-phenylsulfinylphenyl)pyrazolo[1,5-a]-1,3,5-triazine with stirring and the solvent was then distilled off under reduced pressure. After addition of 100 ml of ethyl acetate, the mixture was refluxed for 30 minutes. After cooling, the crystals were recovered by filtration and dried to give sodium (−)-8-(3-methoxy-4-phenylsulfinylphenyl)pyrazolo[1,5-a]-1,3,5-triazine-4-olate dihydrate.

Optical rotation, $[\alpha]_D^{20} = -245°$ (c=0.5, DMF)
Melting point: 228°-235° C. (decomp.)

The same procedure as above was followed using (+)-4-hydroxy-8-(3-methoxy-4-phenylsulfinylphenyl)pyrazolo[1,5-a]-1,3,5-triazine to give sodium (+)-8-(3-methoxy-4-phenylsulfinylphenyl)pyrazolo[1,5-a]-1,3,5-triazine-4-olate dihydrate.

Optical rotation, $[\alpha]_D^{20} = +242°$ (c=0.5, DMF)
Melting point: 228°-235° C. (decomp.)

EXAMPLE 3

The same procedure as Example 2 was followed except that aqueous solutions of lithium hydroxide, potassium hydroxide and calcium hydroxide were respectively used in lieu of aqueous sodium hydroxide solution to give the lithium, potassium and calcium salts of the (−) and (+) forms of 4-hydroxy-8-(3-methoxy-4-phenylsulfinylphenyl)pyrazolo[1,5-a]-1,3,5-triazine.

All of these salts decomposed at or above 220° C.

EXAMPLE 4

In 40 ml of a 1:1 mixture of chloroform and methanol under reflux was dissolved 1 g of (±)-4-hydroxy-8-(3-methoxy-4-phenylsulfinylphenyl)pyrazolo[1,5-a]-1,3,5-triazine and 5 mg of the optically pure (−)-4-hydroxy-8-(3-methoxy-4-phenylsulfinylphenyl)pyrazolo[1,5-a]-1,3,5-triazine obtained in Example 1 was added as seed crystals. The system was allowed to cool under room temperature conditions for 5 hours and the resulting crystals (220 mg) were harvested by filtration.

Optical rotation, $[\alpha]_D^{20} = -45°$ c=0.5, DMF)

The above crop of crystals was recrystallized from chloroform-methanol (1:1) four times to give 44 mg of (−)-4-hydroxy-8-(3-methoxy-4-phenylsulfinylphenyl)-pyrazolo[1,5-a]-1,3,5-triazine with an optical rotation of $[\alpha]_D^{20} = -174°$ (c=0.5, DMF)

The following tests were performed on the salts of optically active triazines of the invention.

TEST EXAMPLE 1

Solubility test

The compounds listed below [the salts of optically active compounds obtained in Examples 2 and 3 and, as control, the corresponding salts of racemic compound] were used as test samples.

Sample I (racemic form)
Sodium (±)-8-(3-methoxy-4-phenylsulfinylphenyl)-pyrazolo[1,5-a]-1,3,5-triazine-4-olate monohydrate
Sample II [(−)-form]
Sodium (−)-8-(3-methoxy-4-phenylsulfinylphenyl)-pyrazolo[1,5-a]-1,3,5-triazine-4-olate dihydrate
Sample III [(+)-form]
Sodium (+)-8-(3-methoxy-4-phenylsulfinylphenyl)-pyrazolo[1,5-a]-1,3,5-triazine-4-olate dihydrate
Sample IV [(−)-form]
Calcium bis[(−)-8-(3-methoxy-4-phenylsulfinylphenyl)pyrazolo[1,5-a]-1,3,5-triazine-4-olate] dihydrate
Sample V [(+)-form]
Calcium bis[(+)-8-(3-methoxy-4-phenylsulfinylphenyl)pyrazolo[1,5-a]-1,3,5-triazine-4-olate] dihydrate Solubility tests with the above respective samples using water (distilled water for injection) and physiological saline as solvents were performed as follows.

Thus, 0.1 g of each sample was put in a 10 ml test tube, followed by addition of an appropriate amount (0.5 ml for the racemic compound or 0.1 ml for the optically active compound) of the solvent (water or physiological saline). Using an incubator (Taiyo Kagaku Kogyo, M-100), the tube was shaken at 25° C. After 4 hours, the content was filtered through a 0.45 μm filter and the filtrate was diluted 100-fold with mobile phase to prepare a test solution. Separately, 40.0 mg of Sample I (racemic form) was accurately weighed and made up with water to make exactly 200 ml. Then, 1 ml of this solution was accurately taken and diluted with mobile phase to make exactly 20 ml (10 μg/ml) of standard solution. Using the above test solutions and the standard solution, the solubilities of the respective samples were determined.

| Apparatus [HPLC (System A)] | |
|---|---|
| Pump | 510 (Waters) |
| Detector | UVIDEC-100-V (Nippon Bunko) |
| Data processor | Data Module 741 (Waters) |
| Auto-sampler | AS-8000 (Tohso) |
| Conditions | |
| Column | TSKgel ODS-120T |
| | (4.6 mm dia. × 150 mm) |
| Mobile phase | acetonitrile-phosphate buffer |
| | (35:65) |
| Flow rate | 1.0 ml/min. |
| Wavelength | 323 nm |
| Injection amount | 20 μl |

The results are shown below in Table 1.

TABLE 1

| Test sample | Water | Physiological saline |
|---|---|---|
| Sample I | 0.221 w/w % | 0.0083 w/w % |
| Sample II | ≧50 w/w % | ≧50 w/w % |
| Sample III | ≧50 w/w % | ≧50 w/w % |
| Sample IV | ≧50 w/w % | ≧50 w/w % |
| Sample V | ≧50 w/w % | ≧50 w/w % |

In the case of Sample II to V, 0.1 g of the bulk substance was completely dissolved in 0.1 ml of the solvent. Therefore, the results were expressed as ≧50 w/w %.

It is clear from Table 1 that the salts of the two isomers are by far more freely soluble in water and physiological saline than the corresponding salt of the racemic compound.

TEST EXAMPLE 2

Xanthine dehydrogenase inhibitory activity test

The test was performed using male ICR rats (aged 6 weeks, b.w. 28.0–40.6 g). The compounds of the invention as obtained in Example 2 were respectively suspended in 0.5% carboxymethylcellulose (CMC) solution and the suspensions were administered orally at the rate of 10 ml/kg (Test Group 1 and Test Group 2). The compound of the invention and its dosage used in each test group are shown below.

Test Group 1
Sodium salt of the optically active triazine compound [(−)-form] obtained in Example 2, 5 mg/kg
Test Group 2
Sodium salt of the optically active triazine compound [(+)-form] obtained in Example 2, 5 mg/kg There was provided a control group treated with 0.5% CMC solution only (control group).

After 4 and 8 hours from the administration, animals in each group were sacrificed, the liver was excised, and the xanthine dehydrogenase activity in the liver was assayed by the following general procedure.

Thus, a homogenate of the liver was diluted 5-fold with 100 mM Tris-HCl buffer (hereinafter referred to merely as buffer). Then, 50 μl of this dilution, 25 μl of a buffer dilution of NAD+ (20 mM) and 25 μl of a buffer solution of potassium oxonate were added to 300 μl of the buffer (the concentrations of NAD+ and potassium oxonate in the total solution were 1 mM each) and the mixture was incubated at 25° C. for 5 minutes. This incubate was centrifuged and the uric acid in the supernatant was estimated by high performance liquid chromatography (HPLC). The value was taken as the pre-treatment baseline.

On the other hand, to a preincubate obtained in the same manner as above was added 100 μl of a buffer solution of xanthine (1 mM) and the mixture was incubated at 25° C. for 5 minutes. The reaction was stopped with 50 μl of 6M perchloric acid and the reaction mixture was centrifuged in the same manner as above. The supernatant was neutralized with an aqueous solution of sodium dihydrogen phosphate and uric acid produced was assayed by HPLC. The value was taken as the post-treatment value.

From the difference between the above post-treatment value and pre-treatment baseline value of uric acid, xanthine dehydrogenase activity was determined. The results are set forth below in Table 2.

TABLE 2

| Group | Enzymatic activity in the liver isolated after 4 hr. (mU/g) | Enzymatic activity in the liver isolated after 8 hr. (mU/g) |
|---|---|---|
| Test group 1 | 7 ± 4** (n = 7) | 17 ± 7** (n = 7) |
| Test group 2 | 33 ± 16** (n = 7) | 22 ± 10** (n = 7) |
| Control group | 152 ± 21 (n = 8) | 137 ± 31 (n = 8) |

In the table, the mark ** denotes p<0.01 with respect to control group.

The following formulation examples illustrate the production of some pharmaceutical compositions using the compounds of the invention.

FORMULATION EXAMPLE 1

| | |
|---|---|
| Sodium (−)-8-(3-methoxy-4-phenyl-sulfinylphenyl)pyrazolo[1,5-a]-1,3,5-triazine-4-olate dihydrate | 100 g |
| Avicel [trademark, maufactured by Asahi Chemical Industry Co., Ltd.] | 40 g |
| Corn starch | 30 g |
| Magnesium stearate | 2 g |
| TC-5 [trademark, manufactured by Shin-Etsu Chemical Co., Ltd., hydroxypropylmethyl cellulose] | 10 g |
| Polyethylene glycol-6000 | 3 g |
| Castor oil | 40 g |
| Ethanol | 40 g |

The sodium (−)-8-(3-methoxy-4-phenylsulfinylphenyl)pyrazolo[1,5-a]-1,3,5-triazine-4-olate dihydrate, Avicel, corn starch and magnesium stearate were milled together and compression-molded using a R 10 mm dragee punch. The resulting tablets were coated with a film coating composition of TC-5, polyethylene glycol 6000, castor oil and ethanol to give film-coated tablets of the above-indicated composition.

FORMULATION EXAMPLES 2 & 3

By the same procedure as followed in Formulation Example 1 except that sodium (+)-8-(3-methoxy-4-phenylsulfinylphenyl)pyrazolo[1,5-a]-1,3,5-triazine-4-olate dihydrate and calcium bis[(−)-8-(3-methoxy-4-phenylsulfinylphenyl)pyrazolo[1,5-a]-1,3,5-triazine-4-olate] dihydrate were respectively used in lieu of sodium (−)-8-(3-methoxy-4-phenylsulfinyphenyl)-pyrazolo[1,5-a]-1,3,5-triazine-4-olate dihydrate to give film-coated tablets.

FORMULATION EXAMPLE 4

| Sodium (−)-8-(3-methoxy-4-phenyl-sulfinylphenyl)pyrazolo[1,5-a]-1,3,5-triazine-4-olate dihydrate | 100 g |
|---|---|
| Crystalline cellulose [J.P.] | 104 g |
| Corn starch [J.P.] | 92 g |
| Talc [J.P.] | 2 g |
| Magnesium stearate [J.P.] | 2 g |

According to the above formula, hard gelatin capsules each containing 100 mg of sodium (−)-8-(3-methoxy-4-phenylsulfinylphenyl)pyrazolo[1,5-a]-1,3,5-triazine-4-olate dihydrate as an active ingredient were manufactured.

Thus, each ingredient was finely divided and the respective powders were evenly mixed together and filled into gelatin capsules for oral administration to give capsules.

FORMULATION EXAMPLE 5

| Sodium (−)-8-(3-methoxy-4-phenyl-sulfinylphenyl)pyrazolo[1,5-a]-1,3,5-triazine-4-olate dihydrate | 350 mg |
|---|---|
| 0.1 N sodium hydroxide | To adjust the pH to 11.5 |
| Distilled water for injection | To make a total of 25 ml |

To a solution of sodium hydroxide in 23 ml of distilled water for injection was added sodium (−)-8-(3-methoxy-4-phenylsulfinylphenyl)pyrazolo[1,5-a]-1,3,5-triazine-1,3,5-triazine-4-olate dihydrate and the solution was adjusted to pH 11.5 with 0.1N aqueous sodium hydroxide solution. The solution was diluted with distilled water for injection to make 25 ml, passed through a bacterial filter and lyophilized. The lyophilizate was aseptically sealed into vials to provide a dry powdery preparation for extemporaneous reconstitution.

This preparation is dissolved in distilled water for injection just before administration to the patient.

FORMULATION EXAMPLES 6 THROUGH 10

The same procedure as Formulation Example 5 was followed except that potassium (−)-8-(3-methoxy-4-phenylsulfinylphenyl)pyrazolo[1,5-a]-1,3,5-triazine-4-olate dihydrate (Formulation Example 6), calcium bis[(−)-8-(3-methoxy-4-phenylsulfinylphenyl)-pyrazolo[1,5-a]-1,3,5-triazine-4-olate] dihydrate (Formulation Example 7), magnesium bis[(−)-8-(3-methoxy-4-phenylsulfinylphenyl)pyrazolo[1,5-a]-1,3,5-triazine-4-olate] dihydrate (Formulation Example 8), (Formulation Example 8), sodium (+)-8-(3-methoxy-4-phenylsulfinylphenyl)pyrazolo[1,5-a]-1,3,5-triazine-4-olate dihydrate (Formulation Example 9), and calcium bis[(+)-8-(3-methoxy-4-phenylsulfinylphenyl)-pyrazolo[1,5-a[-1,3,5-triazine-4-olate] dihydrate (Formulation Example 10) were respectively used in lieu of sodium (−)-8-(3-methoxy-4-phenylsulfinylphenyl)-pyrazolo[1,5-a]-1,3,5-triazine-4-olate dihydrate to give a lyophilized powder for extemporaneous reconstitution.

We claim:

1. A salt selected from group consisting of alkali metal salts and alkaline earth metal salts of an optically active form of a 4-hydroxy-8-(3-lower alkoxy-4-phenyl-sulfinylphenyl)pyrazolo[1,5-a]-1,3,5-triazine of the formula

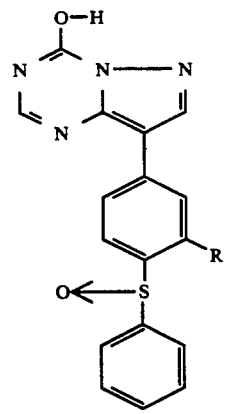

wherein R is a lower alkoxy group.

2. A process for producing an optically active form of a 4-hydroxy-8-(3-lower alkoxy-4-phenylsulfinyl-phenyl)pyrazolo [1,5-a]-1,3,5-triazine of the formula

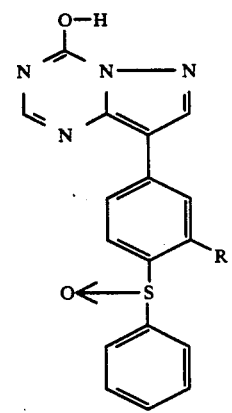

wherein R is a lower alkoxy group or a salt selected from the group consisting of alkali metal salts and alkaline earth metal salts of said optically active form of the compound which comprises reacting a 4-hydroxy-8-(3-lower alkoxy-4-phenylthiophenyl)pyrazolo[1,5-a]-1,3,5-triazine of the formula

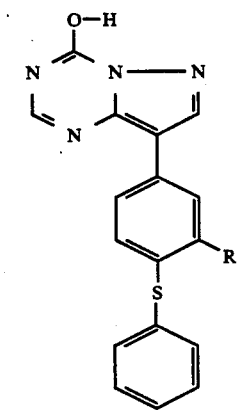

wherein R is a lower alkoxy group with a halogenation agent in the presence of an optically active cyclic secondary alcohol derivative having a substituent R' in the α-position with respect to the hydroxy group wherein R' is a lower alkyl group, a phenyl group or a phenyl-lower alkyl group and either treating the reaction product with water or a metal hydroxide or subjecting the same to heat treatment, if necessary followed by reacting the same with an alkali metal hydroxide or alkaline earth metal hydroxide to give a salt.

3. A process for producing an optically active form of a 4-hydroxy-8-(3-lower alkoxy-4-phenylsulfinylphenyl)pyrazolo[1,5-a]-1,3,5-triazine or a salt selected from the group consisting of alkali metal salts and alkaline earth metal salts of said optically active form of the compound which comprises seeding a solution of the racemic mixture of a 4-hydroxy-8-(3-lower alkoxy-4-phenylsulfinylphenyl)pyrazolo[1,5-a]-1,3,5-triazine with seed crystals composed exclusively of one optically active form of the same triazine compound to cause crystallization of the corresponding optically active form and isolating the resulting crystals, if necessary followed by treating the same with an alkali metal hydroxide or alkaline earth metal hydroxide to give a salt.

4. A pharmaceutical composition having xanthine oxidase inhibitory activity which comprises an effective amount of the salt of claim 1 together with a pharmaceutically acceptable nontoxic carrier.

5. A pharmaceutical composition according to claim 4 which is an antipodagric agent.

6. A pharmaceutical composition according to claim 4 which is in the form of an injectable solution.

7. A method for treating gout in a patient which comprises administering to said patient an effective amount of the salt of claim 1.

8. A pharmaceutical composition according to claim 5 which is in the form of an injectable solution.

9. A process according to claim 2, wherein said halogenation agent is at least one compound selected from the group consisting of t-butyl-hypochlorite, 1-chlorobenzotriazole and N-chlorosuccinimide.

10. A process according to claim 2, wherein said optically active cyclic secondary alcohol derivative has a 4- to 8-membered ring.

11. A process according to claim 10, wherein said ring contains a hetero atom.

12. A process according to claim 2, wherein said optically active cyclic secondary alcohol derivative has a 5- to 6-membered ring.

13. A process according to claim 2, wherein said optically active cyclic secondary alcohol derivative is selected from the group consisting of (−)-menthol, (+)-menthol, (−)-8-phenylmenthol, (+)-8-phenylmenthol, (+)-2-tert-butyl-1-indanol, (−)-borneol, [(1S)-endo]-(−)-borneol, (1S,2S)-(+)-1-hydroxy-2-methyl-3-cyclopentene, (1S,2S)-(+)-1-hydroxy-2-methylcyclohexane, (1S,2R)-(+)-1-hydroxy-2-phenylcyclohexane, (1S,2R)-(+)-1-hydroxy-2-phenylcyclopentane and (1S,2R)-(+)-3-hydroxy-2-phenyltetrahydrofuran.

14. A salt selected from the group consisting of alkali metal salts and alkaline earth metal salts of an optically active form of a 4-hydroxy-8-(3-lower alkoxy-4-phenylsulfinylphenyl)pyrazolo[1,5-a]-1,3,5-triazine of the formula

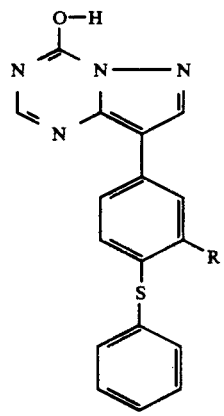

wherein R is a lower alkoxy group produced by
(a) reacting a 4-hydroxy-8-(3-lower alkoxy-4-phenylsulfinylphenyl)pyrazolo[1,5-a]-1,3,5-triazine of the formula

wherein R is a lower alkoxy group with a halogenation agent in the presence of an optically active cyclic secondary alcohol derivative having a substituent R' in the α-position with respect to the hydroxy group, wherein R' is a lower alkyl group, a phenyl group or a phenyl-lower alkyl group,
(b) treating the reaction product with water or a metal hydroxide or subjecting the same to heat treatment, and
(c) reacting the product from (b) with an alkali metal hydroxide or alkaline earth metal hydroxide to give a salt.

* * * * *